US008463399B2

(12) United States Patent
Polkinghorne et al.

(10) Patent No.: US 8,463,399 B2
(45) Date of Patent: Jun. 11, 2013

(54) OVERMOLDED COMPONENTS FOR IMPLANTABLE MEDICAL LEADS AND RELATED METHODS

(75) Inventors: Jeannette C. Polkinghorne, St. Anthony, MN (US); Joseph A. Cihlar, East Bethel, MN (US); Mitchell L. Horn-Wyffels, New Hope, MN (US); Joseph J. Nelsen, Forest Lake, MN (US); Raymond Gessler, Roberts, WI (US); Erin K. Webb, Minneapolis, MN (US); Joseph J. Schachtner, St. Paul, MN (US); Arienne P. Simon, Lino Lakes, MN (US); Andrew De Kock, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 856 days.

(21) Appl. No.: 12/607,806

(22) Filed: Oct. 28, 2009

(65) Prior Publication Data
US 2010/0125320 A1 May 20, 2010

Related U.S. Application Data

(60) Provisional application No. 61/116,588, filed on Nov. 20, 2008.

(51) Int. Cl.
*A61N 1/05* (2006.01)
(52) U.S. Cl.
USPC .......................................... 607/116; 607/120
(58) Field of Classification Search
USPC .................... 607/116, 120, 121, 126, 130
See application file for complete search history.

(56) References Cited

U.S. PATENT DOCUMENTS

| 4,550,737 A | * | 11/1985 | Osypka ........................ 607/127 |
| 4,628,944 A | | 12/1986 | MacGregor et al. |
| 4,819,661 A | | 4/1989 | Heil, Jr. et al. |
| 4,819,662 A | | 4/1989 | Heil, Jr. et al. |
| 5,489,294 A | | 2/1996 | McVenes et al. |
| 5,531,780 A | | 7/1996 | Vachon |
| 5,545,206 A | | 8/1996 | Carson |
| 5,562,723 A | | 10/1996 | Rugland et al. |

(Continued)

FOREIGN PATENT DOCUMENTS

| WO | WO 01/45791 A1 | 6/2001 |
| WO | WO 2005/039691 | 5/2005 |
| WO | WO 2007/059386 | 5/2007 |

OTHER PUBLICATIONS

International Search Report and Written Opinion issued in PCT/US2011/026644, mailed May 23, 2011, 15 pages.

(Continued)

*Primary Examiner* — Carl H Layno
*Assistant Examiner* — Luther Behringer
(74) *Attorney, Agent, or Firm* — Faegre Baker Daniels LLP

(57) ABSTRACT

The various embodiments disclosed herein relate to medical electrical leads. More specifically, certain embodiments relate to leads having one or more drug-eluting components that are overmolded or otherwise positioned on the lead. Other embodiments relate to leads having one or more patterned surfaces, including some leads with one or more patterned surfaces over which one or more drug-eluting components are positioned. Further implementations relate to leads having one or more overmolded patterned surfaces, including some embodiments in which the overmolded surfaces contain at least one drug-eluting component.

23 Claims, 12 Drawing Sheets

U.S. PATENT DOCUMENTS

| | | | |
|---|---|---|---|
| 5,662,697 A | 9/1997 | Li et al. | |
| 5,697,964 A | 12/1997 | Gates | |
| 5,713,945 A | 2/1998 | Fischer et al. | |
| 5,755,767 A | 5/1998 | Doan et al. | |
| 5,766,527 A | 6/1998 | Schildgen et al. | |
| 5,824,030 A | 10/1998 | Yang et al. | |
| 5,833,715 A | 11/1998 | Vachon et al. | |
| 5,853,652 A | 12/1998 | Schildgen et al. | |
| 5,902,329 A * | 5/1999 | Hoffmann et al. | 607/121 |
| 5,931,864 A | 8/1999 | Chastain et al. | |
| 5,987,746 A | 11/1999 | Williams | |
| 5,991,668 A | 11/1999 | Leinders et al. | |
| 6,038,482 A | 3/2000 | Vachon | |
| 6,192,280 B1 | 2/2001 | Sommer et al. | |
| 6,253,110 B1 | 6/2001 | Brabec et al. | |
| 6,263,249 B1 * | 7/2001 | Stewart et al. | 607/116 |
| 6,298,272 B1 | 10/2001 | Peterfeso et al. | |
| 6,304,786 B1 | 10/2001 | Heil, Jr. et al. | |
| 6,360,129 B1 | 3/2002 | Ley et al. | |
| 6,361,780 B1 | 3/2002 | Ley et al. | |
| 6,363,286 B1 | 3/2002 | Zhu et al. | |
| 6,363,287 B1 | 3/2002 | Brabec et al. | |
| 6,385,491 B1 | 5/2002 | Lindemans et al. | |
| 6,405,091 B1 | 6/2002 | Vachon et al. | |
| 6,459,937 B1 | 10/2002 | Morgan et al. | |
| 6,549,812 B1 | 4/2003 | Smits | |
| 6,716,444 B1 * | 4/2004 | Castro et al. | 424/422 |
| 6,766,203 B2 | 7/2004 | Doan et al. | |
| 6,889,092 B2 | 5/2005 | Zhu et al. | |
| 7,013,181 B2 | 3/2006 | Westlund | |
| 7,174,221 B1 | 2/2007 | Chen et al. | |
| 7,184,839 B2 | 2/2007 | Clemens et al. | |
| 7,239,923 B1 | 7/2007 | Tockman et al. | |
| 7,272,448 B1 | 9/2007 | Morgan et al. | |
| 7,337,011 B2 | 2/2008 | Stokes et al. | |
| 7,630,761 B2 | 12/2009 | Salo et al. | |
| 7,953,499 B2 | 5/2011 | Knapp et al. | |
| 2003/0028231 A1 | 2/2003 | Partridge et al. | |
| 2003/0093136 A1 | 5/2003 | Osypka et al. | |
| 2003/0163171 A1 | 8/2003 | Kast et al. | |
| 2004/0172117 A1 | 9/2004 | Hill et al. | |
| 2004/0230272 A1 | 11/2004 | Cates et al. | |
| 2004/0230273 A1 | 11/2004 | Cates et al. | |
| 2004/0230274 A1 | 11/2004 | Heil et al. | |
| 2004/0260397 A1 | 12/2004 | Lambrecht et al. | |
| 2005/0070985 A1 | 3/2005 | Knapp et al. | |
| 2005/0070988 A1 | 3/2005 | Kawula et al. | |
| 2005/0245884 A1 | 11/2005 | Deininger | |
| 2005/0267556 A1 | 12/2005 | Shuros et al. | |
| 2006/0041296 A1 | 2/2006 | Bauer et al. | |
| 2006/0121084 A1 | 6/2006 | Borden et al. | |
| 2006/0134071 A1 | 6/2006 | Ross et al. | |
| 2006/0134079 A1 | 6/2006 | Sih et al. | |
| 2006/0136027 A1 | 6/2006 | Westlund et al. | |
| 2006/0136028 A1 | 6/2006 | Ross et al. | |
| 2006/0204717 A1 | 9/2006 | Deininger et al. | |
| 2006/0235499 A1 | 10/2006 | Heil, Jr. et al. | |
| 2006/0282120 A1 | 12/2006 | Sih | |
| 2007/0051531 A1 | 3/2007 | Borgaonkar et al. | |
| 2007/0100348 A1 | 5/2007 | Cauthen, III et al. | |
| 2007/0288040 A1 | 12/2007 | Ferree | |
| 2007/0293922 A1 | 12/2007 | Soltis et al. | |
| 2007/0299491 A1 | 12/2007 | Borgaonkar et al. | |
| 2008/0027526 A1 | 1/2008 | Zarembo | |
| 2008/0057784 A1 | 3/2008 | Zarembo et al. | |
| 2008/0077217 A1 | 3/2008 | Santamore et al. | |
| 2009/0024197 A1 | 1/2009 | Jensen | |
| 2009/0054961 A1 | 2/2009 | Borgaonkar et al. | |
| 2009/0233491 A1 | 9/2009 | Barker et al. | |
| 2009/0264943 A1 | 10/2009 | Barker | |
| 2010/0004723 A1 | 1/2010 | Foster et al. | |
| 2010/0016889 A1 | 1/2010 | Ferree | |
| 2010/0125320 A1 | 5/2010 | Polkinghorne et al. | |
| 2011/0160831 A1 | 6/2011 | De Kock et al. | |

OTHER PUBLICATIONS

International Search Report and Written Opinion issued in PCT/US2009/062393, mailed Mar. 12, 2010, 16 pages.

International Search Report and Written Opinion issued in PCT/US2010/052876, mailed Mar. 2, 2011.

* cited by examiner

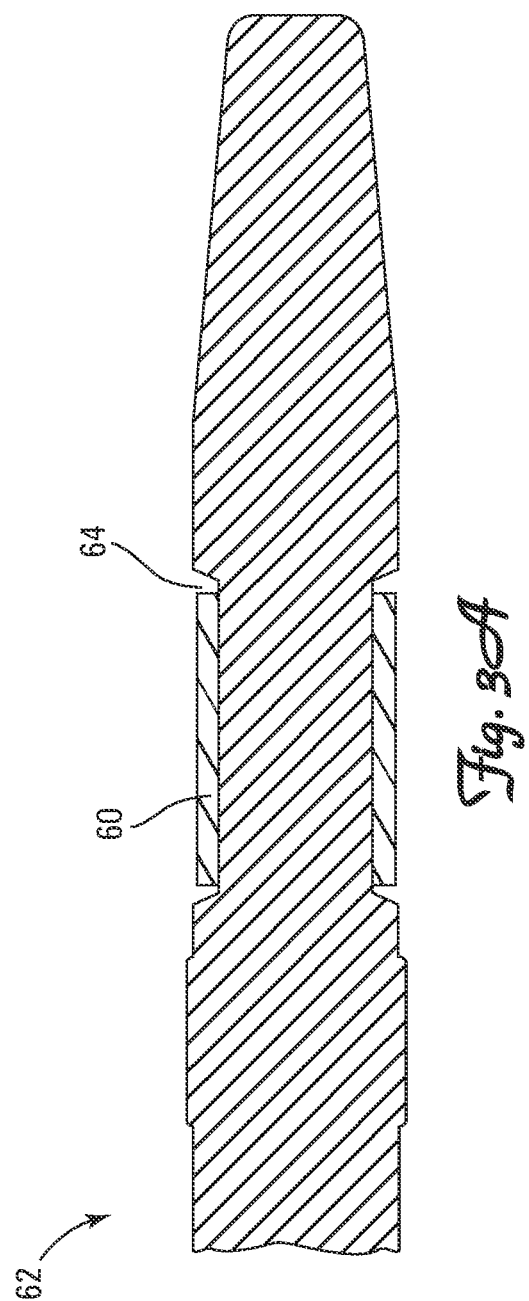

OVERMOLDED COMPONENTS FOR IMPLANTABLE MEDICAL LEADS AND RELATED METHODS

CROSS-REFERENCE TO RELATED APPLICATION

This application claims priority under 35 U.S.C. §119 to U.S. Provisional Application No. 61/116,588, filed on Nov. 20, 2008, entitled "Overmolded Components for Implantable Medical Leads and Related Methods," which is incorporated herein by reference in its entirety for all purposes.

TECHNICAL FIELD

The embodiments disclosed herein relate to body implantable medical devices, and more particularly, to medical electrical leads.

BACKGROUND

Various types of medical electrical leads for use in cardiac rhythm management systems are known. Such leads are typically extended intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explantation procedures. There is a continuing need for improved lead designs.

SUMMARY

One embodiment disclosed herein relates to an implantable medical lead. The lead has an electrode, a lead body coupled to the electrode, and an overmolded component. The lead body has a recess adjacent to the electrode and the overmolded component is formed in the recess. In one alternative, the overmolded component is a drug-eluting overmolded collar. In another alternative, the component is a plug, strip, spiral, dot, or tines.

Another embodiment relates to an implantable medical lead having an electrode and a lead body coupled to the electrode. The lead body has an outer surface and a patterned structure. In this embodiment, the patterned structure is formed on the outer structure of the lead body and comprises patterned recesses. The patterned structure is configured to enhance fixation of the lead body to a tissue. In one alternative, a drug-eluting material is positioned within the patterned recesses.

A further implementation relates to an implantable medical lead having an electrode and a lead body coupled to the electrode. The lead body has an outer surface, a patterned surface, and an overmolded component. The patterned surface is formed in the outer surface of the lead body and has patterned recesses. The patterned structure is configured to enhance fixation of the lead body to a tissue. The overmolded component is formed in a portion of the patterned recesses substantially adjacent to the electrode.

Another implementation relates to a method of forming an implantable medical electrical lead having an elongated polymeric body with an outer surface. The method includes forming a plurality of patterned recesses in the outer surface of the lead body and overmolding a first drug-eluting component at least partially within a first of the patterned recesses. In one alternative, the forming the plurality of patterned recesses includes applying laser energy to selectively remove material from the outer surface of the lead body. In another alternative, the method further includes overmolding a second drug-eluting component at least partially within a second of the patterned recesses.

A further embodiment relates to a method of forming an implantable medical electrical lead having an elongated polymeric body with an outer surface. The method includes disposing a first drug-eluting component on the outer surface of the lead body and forming a patterned surface on the outer surface of the lead body, wherein at least a portion of the patterned surface comprises the first drug-eluting component. In one alternative implementation, disposing the first drug-eluting component on the outer surface includes overmolding the first drug-eluting component onto the outer surface.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3A is a cross-sectional view of a lead body with a drug-eluting collar, according to one embodiment.

DETAILED DESCRIPTION

Various embodiments disclosed herein relate to a medical electrical lead having an overmolded or premolded drug-eluting component. Other embodiments relate to a medical electrical lead having a patterned surface on the lead body. Further embodiments relate to leads having both a patterned surface and a drug-eluting component that is overmolded onto or premolded and then placed on a portion of the patterned surface.

The leads according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate bi-ventricular pacing in a CRT or CRT-D system. Still additionally, leads formed according to embodiments of the present invention may be configured to be secured to an exterior surface of the heart (i.e., as epicardial leads).

Figure 1:
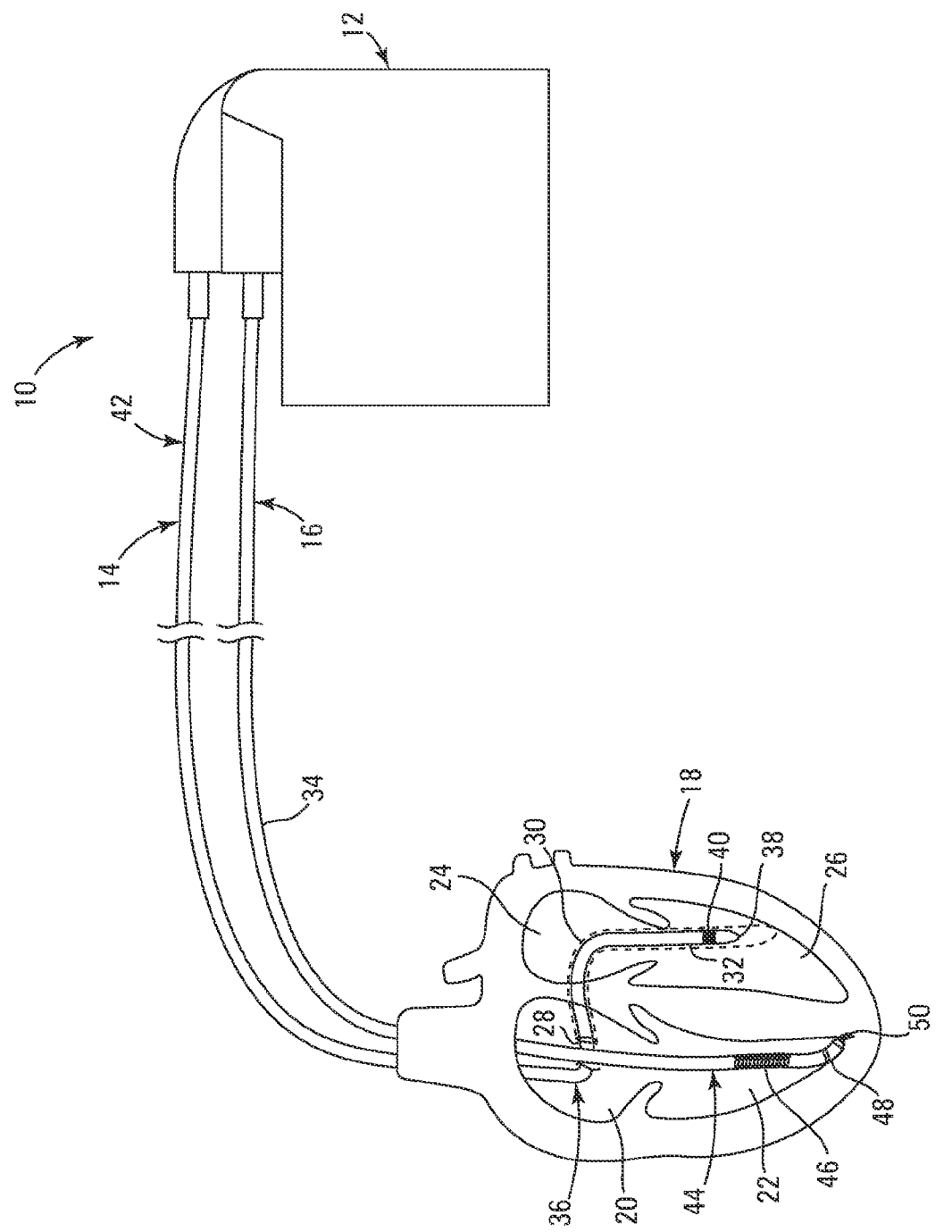
FIG. 1 is a schematic drawing of a cardiac rhythm management system including a pulse generator coupled to two leads deployed in a patient's heart, according to one embodiment.

FIG. 1 is a schematic drawing of a cardiac rhythm management system 10 including a pulse generator 12 coupled to a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30.

According to one embodiment, as shown in FIG. 1, lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes a distal end 38 and an electrode 40 both positioned within the branch vessel 32. The illustrated position of the lead 14 may be used for delivering a pacing stimulus to the left side of the heart 18. Additionally, it will be appreciated that the lead 14 may also be partially deployed in other regions of the coronary venous system, such as in the great cardiac vein or other branch vessels for providing therapy to the left side or right side of the heart 18.

In the illustrated embodiment, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown, in the illustrated embodiment, the lead 16 includes a proximal portion 34 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. As will be appreciated, the high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

In various embodiments, the lead 16 includes additional defibrillation/cardioversion and/or additional pace/sense electrodes positioned along the lead 16 so as to provide multi-polar defibrillation/cardioversion capabilities. In one exemplary embodiment, the lead 16 includes a proximal high voltage electrode in addition to the electrode 46 positioned along the lead 16 such that it is located in the right atrium 20 (and/or superior vena cava) when implanted. As will be appreciated, additional electrode configurations can be utilized with the lead 16. In short, any electrode configuration can be employed in the lead 16 without departing from the intended scope of the present invention.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, a cardiac resynchronization (CRT) device configured for bi-ventricular pacing, and/or includes combinations of pacing, CRT, and defibrillation capabilities.

Figure 2:
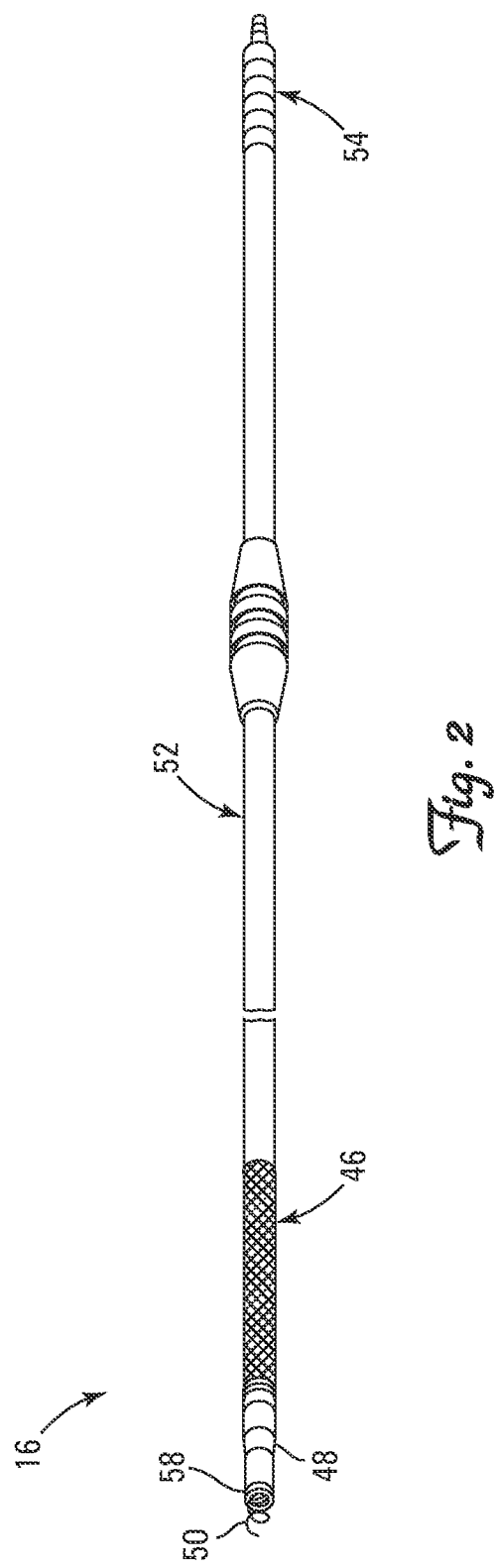
FIG. 2 is a perspective view of one of the leads shown in FIG. 1 according to one embodiment.

FIG. 2 is a perspective view of the lead 16 shown in FIG. 1. As discussed above, the lead 16 is adapted to deliver electrical pulses to stimulate a heart and/or for receiving electrical pulses to monitor the heart. The lead 16 includes an elongated polymeric lead body 52, which may be formed from any polymeric material such as polyurethane, silicone rubber, or the like.

As further shown, the lead 16 further includes a connector 54 operatively associated with the proximal end of the lead body 52. The connector 54 is configured to mechanically and electrically couple the lead 16 to the pulse generator 12, and may be of any standard type, size or configuration. As will be appreciated, the connector 54 is electrically and mechanically connected to the electrodes 46, 48, 50 by way of one or more conducting wires (not shown) within the lead body 52. The conducting wires utilized may take on any configuration providing the necessary functionality. For example, as will be appreciated, the conducting wires coupling the electrodes 48 and/or 50 to the connector 54 (and thus, to the pulse generator 12) may be coiled conductors defining an internal lumen for receiving a stylet or guidewire for lead delivery. Conversely, in various embodiments, the conducting wire to the high voltage electrode 46 may be a multi-strand cable conductor.

In addition, the lead 16 also includes a drug-eluting component 58. In certain embodiments, the drug-eluting component 58 is positioned at or near the distal end of the lead 16. However, it is understood that the drug-eluting component 58 can be located anywhere along the length of the lead 16. It is further understood that the lead 16 can have one or more drug-eluting components. When the lead 16 is implanted, the drug-eluting component 58 may elute a bioactive agent that suppresses the inflammatory response and/or other unwanted biological processes associated with implantation and the presence of the foreign object. In addition, the bioactive agent could also reduce the growth of non-excitable, connective tissue and/or prevent myocyte cell function impairment and/or necrosis around or near the electrode (e.g., the capsule).

According to one embodiment, the drug-eluting component is a collar. Alternatively, the component can take the form of one or more plugs, strips, spirals, dots, tines, or any other known shapes or configurations that could be used to deliver a bioactive agent to the patient.

FIG. 3A depicts one embodiment of a drug-eluting component 60. In this embodiment, the component 60 is an overmolded drug-eluting collar disposed in a recessed portion 64 of the lead body 62. Alternatively, as explained above, the drug-eluting component 60 can be overmolded or premolded and can be positioned anywhere along the length of the lead body 62. In a further alternative, more than one drug-eluting component 60 can be positioned along the length of the lead body 62.

Figure 3B:
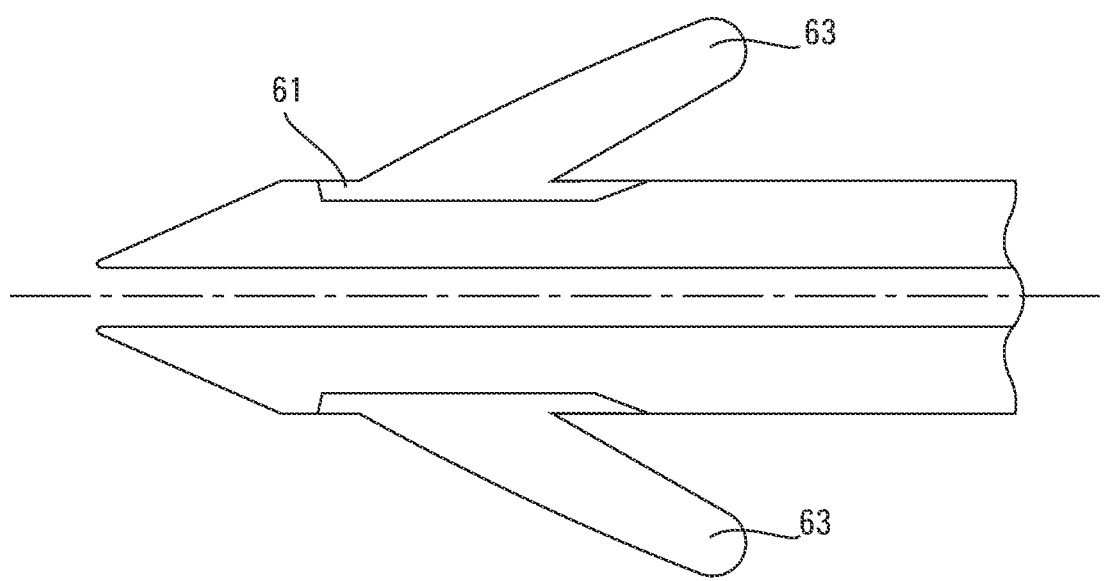
FIG. 3B is a cross-sectional view of a lead body with a drug-eluting component having tines, according to one embodiment.

FIG. 3B depicts an alternative implementation of a drug-eluting component 61. In this embodiment, the component 61 is an overmolded drug-eluting component having tines 63.

In accordance with one embodiment, the drug-eluting component 60 has an exposed surface area that ranges in size from about 0.1 cm$^2$ to about 5 cm$^2$. Alternatively, the surface area ranges from about 0.03 cm$^2$ to about 0.3 cm$^2$.

According to one implementation, the drug-eluting component 60 is a combination of a polymer and an agent, which can be any drug or bioactive agent. For example, in one embodiment the polymer is liquid silicone rubber ("LSR") and the drug is dexamethasone acetate ("DXA"). DXA is an anti-inflammatory agent. Alternatively, the drug-eluting component 60 can have more than one bioactive agent.

The polymer, according to one embodiment, can include, but is not limited to, one or more of the following polymers: Solef® (Solef® 21508 polymer); polyvinylidene-hexafluoropropylene or poly(VF2-co-HFP) from Solvay, Brussels, Belgium; acetoxy cure, Room-Temperature-Vulcanizing (RTV) silicone elastomers; UV curable silicone; UV curable polymer; platinum catalyzed addition cure liquid silicone rubber; styrene isobutylene styrene (SIBS); peroxide cure silicone rubber; Nafion; silicone (including LSR), polymers based on the structural unit R$_2$SiO, where R is an organic group; medical adhesives; cyanoacrylates; Rehau 1511; ethylene vinyl alcohol (E/VAL; a thermoplastic polymer); polyethylene glycol (PEG); polyvinyl alcohol; polyvinyl propylene; hyaluronic acid; polyacrylamides; polycaprolactone, polylactide (PLA); polyglycolide (PGA); poly(lactide-co-glycolide) (PLGA); polyurethane; polymethylmethacrylates; polyethylene; polyvinylpyrrolidone; polyacrylic acid; poly (2-hydroxyethyl methacrylate); pHEMA polyacrylamide; polyethylene-co-vinyl acetate; polyanhydrides; polyorthoesters; polyimides; polyamides; polyanhydrides; polyetherketones; polyaryletherketones; polysiloxane urethanes; polyisobutylene copolymers; and copolymers and combinations thereof.

The bioactive agent can be any drug or bioactive agent which can serve as a useful therapeutic, prophylactic, or even diagnostic agent when released into the patient. Exemplary bioactive agents include, but are not limited to, the following: an anti-inflammatory; anti-proliferative; anti-arrhythmic; anti-migratory; anti-neoplastic; antibiotic; anti-restenotic; anti-coagulation; anti-infectives; anti-oxidants; anti-macrophagic agents (e.g., bisphosphonates); anti-clotting (e.g., heparin, coumadin, aspirin); anti-thrombogenic; immunosuppressive agents; an agent that promotes healing, such as a steroid (e.g., a glucocorticosteroid) and/or re-endothelialization; and combinations thereof.

More specifically, the one or more bioactive agents may include, but are not limited to, the following: paclitaxel; clobetasol proprionate; rapamycin; sirolimus; everolimus; tacrolimus; actinomycin-D; dexamethasone (e.g., dexamethasone, dexamethasone sodium phosphate or dexamethasone acetate); betamethasone; mometasone furoate; vitamin E; mycophenolic acid; cyclosporins; beclomethasone (e.g., beclomethasone dipropionate anhydrous); their derivatives, analogs, salts; and combinations thereof. Additionally, the one or more bioactive agents may include bisphosphonates. Bisphosphonates inhibit macrophage-like action, thereby limiting the local inflammatory response. According to yet other embodiments, the one or more bioactive agents may include non-steroidal anti-inflammatory agents such as aspirin, ibuprofen, acetaminophen, and COX inhibitors (e.g., celecoxib and/or diclofenac).

According to another embodiment, the one or more bioactive agents can include one or more diagnostic agents such as, for example, radio opaque materials such as barium sulfate, platinum powder, tungsten powder, zirconium dioxide, bismuth trioxide and/or bismuth subcarbonate. In one embodiment, the one or more diagnostic agents can be combined with one or more other bioactive agents. Alternatively, the one or more diagnostic agents need not be combined with any other agents.

The bioactive agent can be present in the drug-eluting component in any effective amount. An "effective amount" generally means an amount which provides the desired local or systemic effect. For example, an effective dose is an amount sufficient to affect a beneficial or desired clinical result. The precise determination of what would be considered an effective dose may be based on factors individual to each patient, including their size and age. In one embodiment, the therapeutic agent is present in a concentration ranging from about 1 µg/cm$^2$ to about 20 mg/cm$^2$. Alternatively, the agent is present in a concentration ranging from about 1 to about 20 mg/cm$^2$. In a further alternative, the agent may also be present at a concentration of higher than about 20 mg/cm$^2$.

The drug-eluting component can be formed such that it includes an effective drug to polymer ratio (D:P). The drug to polymer ratio (D:P) can be selected for specific release properties. The release rate of the drug from the component can be manipulated through selection of an appropriate drug to polymer ratio to achieve the desired drug release profile. The drug to polymer ratio in the component can be selected such that the drug release profile is immediate, short term, or sustained release. A drug-eluting component having an immediate release profile releases the drug content within minutes to about an hour after implantation. A drug-eluting component having a short term release profile more slowly liberates the content within days to weeks following implantation. Finally, a drug-eluting component having a sustained release profile releases the content very slowly, with full release requiring months to years. According to one embodiment, the drug to polymer ratio in the drug-eluting component can be selected such that it ranges from 1:50 to 1:1. According to another embodiment, the drug to polymer ratio in the drug-eluting component can be selected such that it ranges from 1:10 to 1:1. Typically, a drug-eluting component including a higher drug to polymer ratio will have a faster drug release profile. Additionally, the selection of the polymer included in the component can also affect the release rate of the drug.

In one embodiment, the drug-eluting component is manufactured by mixing the polymer and the agent together. For example, one implementation calls for mixing the polymer(s) and the bioactive agent(s) together to produce the drug-eluting component. In one embodiment in which the polymer is LSR and the bioactive agent is DXA, the LSR is provided in liquid form and the DXA is provided in powder form.

Figure 4:
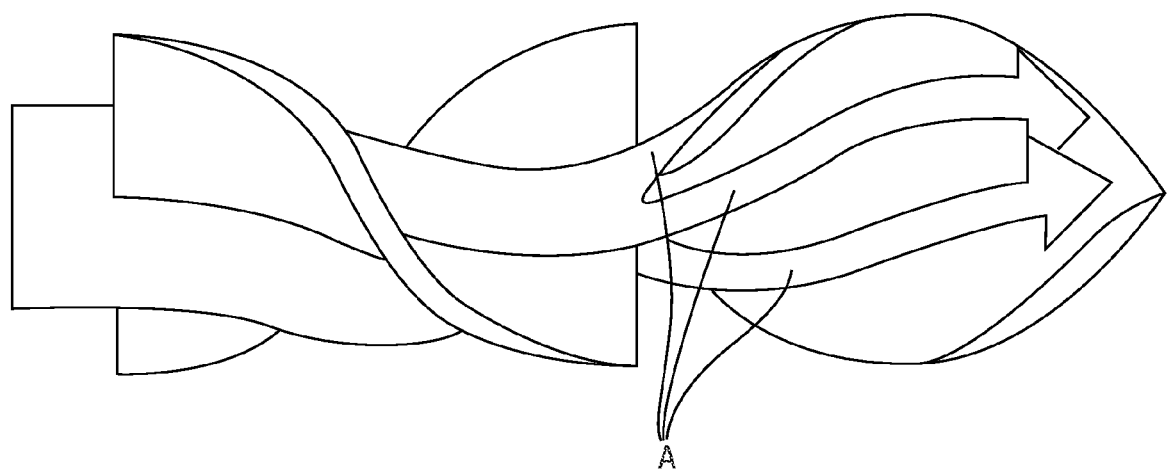
FIG. 4 is a schematic drawing of a mixer element, according to one embodiment.

Regardless of the specific components, the polymer and bioactive agent are typically combined and mixed together in a mixer. In one embodiment, the mixer is a static mixer. It is understood in the art that a static mixer is a device for blending or mixing at least two materials. The mixer has mixer elements disposed within a cylindrical or squared housing. In use, the materials to be mixed are delivered into and through the mixer. As the materials flow through the mixer, the non-moving mixer elements disposed within the cylinder cause the materials to blend or mix together. One example of a mixer element 68 is shown in FIG. 4. As shown in that figure, the materials flow through the cylindrical housing (not shown) and around/over the mixer element 68 as shown by the arrows A.

The extent of mixing is impacted by the mixer length, the inner diameter of the housing, the number of mixer elements, the mixer element design, and flow rate.

In one aspect, a static mixer can allow for a more homogenous component mixture than can typically be achieved by other types of mixers. Such homogeneity results in sturdier molded components with less variation, thereby allowing for components with thinner walls and more uniform drug distribution, thereby leading to more repeatable drug release.

Alternatively, the mixer can be a centrifugal mixer. In a further alternative, a liquid injection system is provided (similar to the system disclosed below) that includes a mixer for mixing the components. According to a further implementation, the mixing can be accomplished using continuous line mixing, which is also known as meter mixing. The mixing can also be accomplished in another embodiment using acoustic mixing. In yet another alternative, any known mixer can be used.

In one embodiment, the quantity of the components that are mixed together can range from about 1 g to about 100 kg. Alternatively, in one implementation using a centrifugal mixer, the components range in amount from about 10 g to about 1 kg. In a further alternative using a static or continuous mixer, the components range in amount from about 1 kg to about 100 kg.

In one implementation in which a centrifugal or other type of rotating mixer is used, the components are mixed together at a rate ranging from about 700 rpm to about 3500 rpm for a period ranging from about 10 seconds to about 10 minutes. Alternatively, the components are mixed together by a mixer running at a rate ranging from about 1700 rpm to about 2500 rpm. In another alternative, the components are mixed together for a period ranging from about 30 seconds to about 2 minutes.

In a further alternative, the components are mixed together in a process that utilizes both types of mixers. That is, according to one embodiment, the components are first mixed in a centrifugal mixer and then subsequently mixed in a static mixer. Alternatively, the components can be first mixed in a static mixer and then subsequently mixed in a centrifugal mixer.

In accordance with one implementation, the components are mixed in two stages. In the first stage, a first portion of the polymer and a first portion of the bioactive agent are added to the mixer and mixed together. In the subsequent second stage, a second portion of the polymer and a second portion of the bioactive agent are added and mixed together. In one embodiment, a centrifugal mixer is used, and the materials of the first stage are mixed together for from about 10 seconds to about 10 minutes, or alternatively from about 30 seconds to about 2 minutes. Subsequently, the materials of the second stage are mixed together for from about 10 seconds to about 10 minutes, or alternatively from about 30 seconds to about 2 minutes. In one embodiment, the two portions of the mixture are then further mixed in a static mixer.

Alternatively, the components are mixed in two stages in a static mixer. In a further alternative, the mixture is then further mixed in a centrifugal mixer.

Figure 5A:
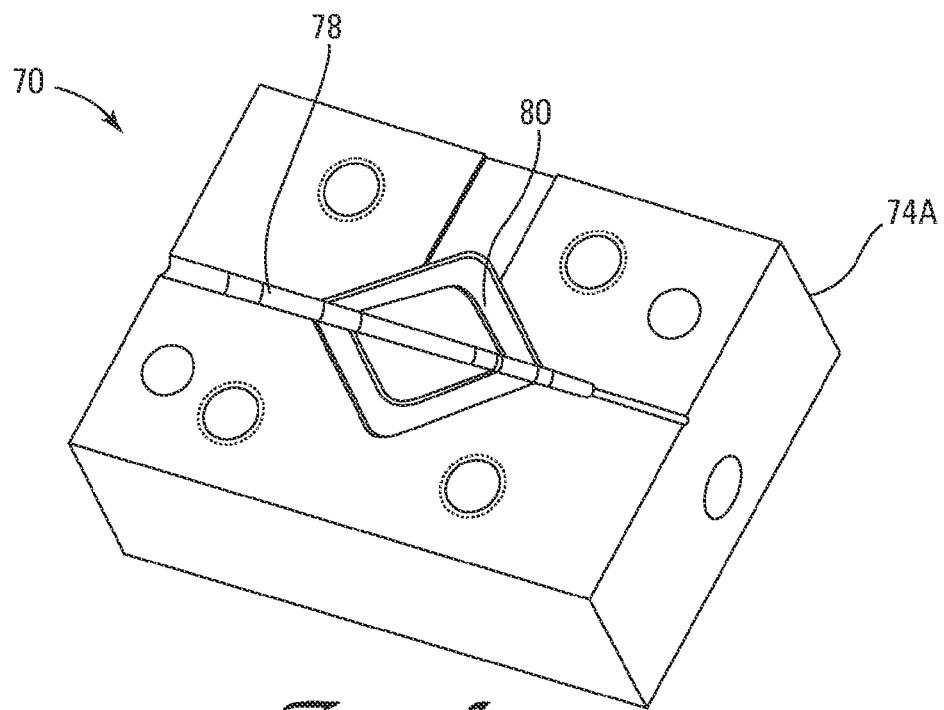
FIG. 5A is a perspective view of the bottom half of a mold, according to one embodiment.
Figure 5B:
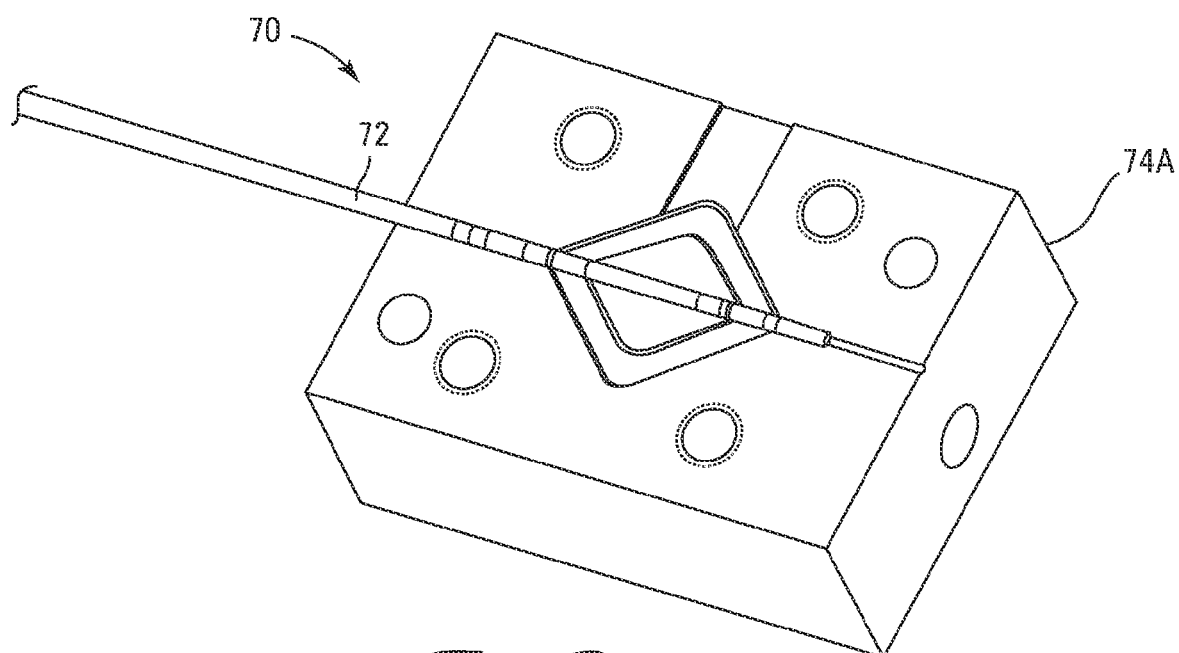
FIG. 5B is a perspective view of the bottom half of the mold of FIG. 5A and a lead body, according to one embodiment.
Figure 5C:
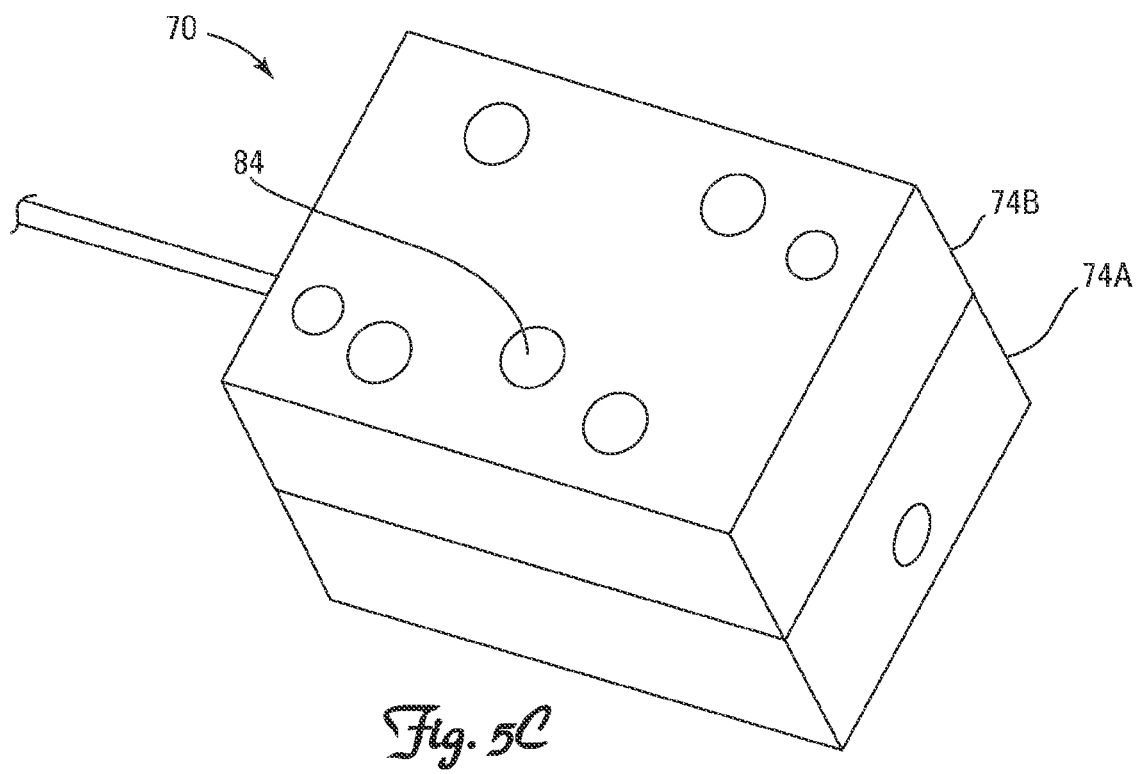
FIG. 5C is a perspective view of the top half combined with the bottom half of the mold of FIG. 5A and a lead body, according to one embodiment.
Figure 5D:
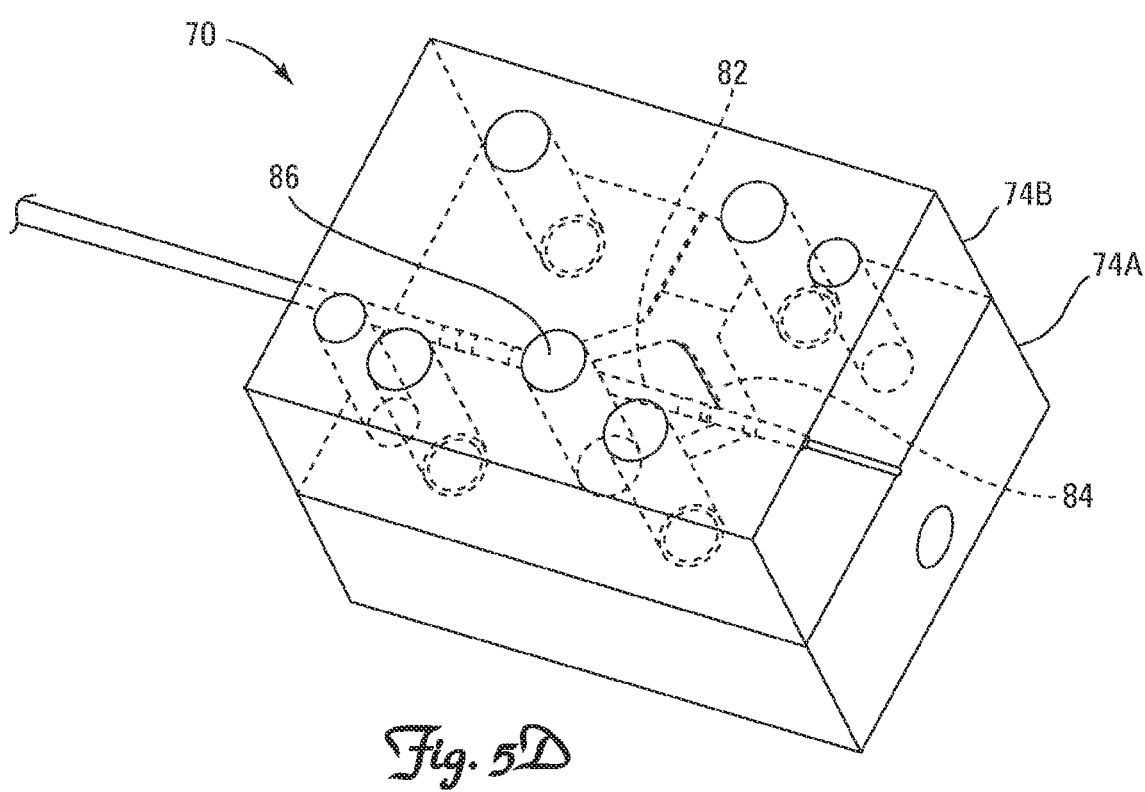
FIG. 5D is a perspective view of the top half combined with the bottom half of the mold of FIG. 5A and a lead body, according to one embodiment.
Figure 5E:
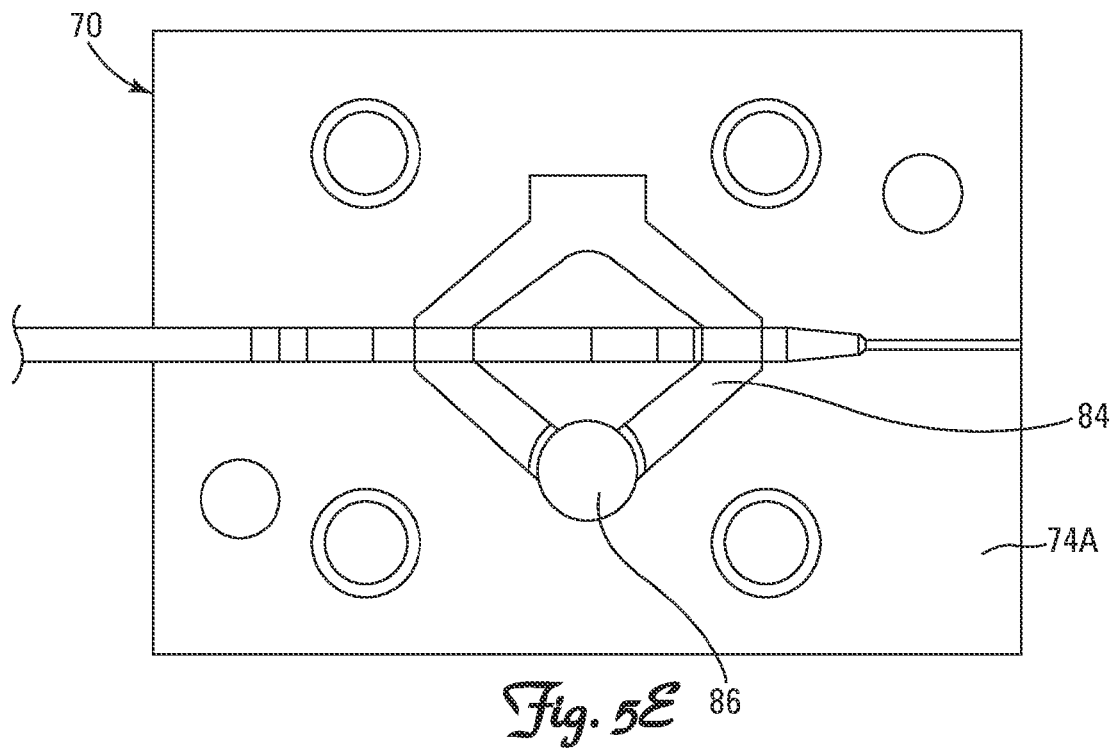
FIG. 5E is a top view of the bottom half of the mold of FIG. 5A, according to one embodiment.
Figure 5F:
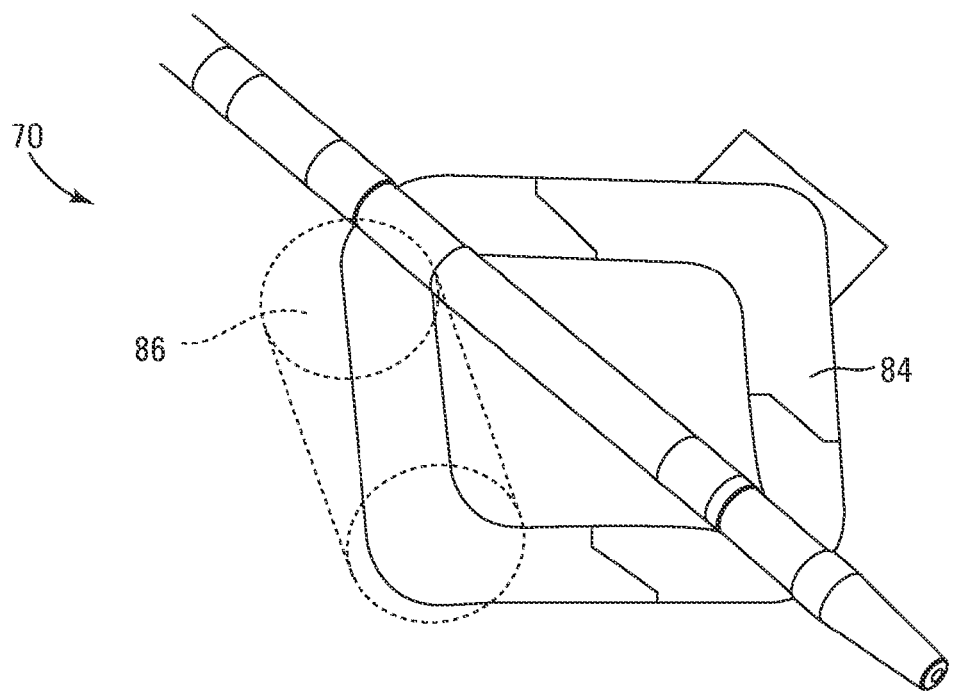
FIG. 5F is an expanded perspective view of the bottom half of the mold of FIG. 5A, according to one embodiment.

When the mixing is complete, according to one embodiment, the liquid mixture is added to a mold containing a lead body, such as the exemplary mold 70 and lead body 72 as depicted in FIGS. 5A-5F. In this embodiment, as best shown in FIGS. 5C and 5D, the mold 70 has two halves: a first (or lower) half 74A and a second (or upper) half 74B.

FIG. 5A depicts the lower half 74A of the mold 70 in its uncoupled configuration in which the halves 74A, 74B are not coupled, according to one implementation. The lower half 74A defines recesses and holes along its contact face 76. The recesses in the lower half 74A are a lead receiving recess 78 and an overmolding recess 80. It is understood that the contact face (not shown) of the upper half 74B has identical recesses that, when the two halves are coupled together as shown in FIGS. 5C and 5D, match up the recesses defined in the lower half 74A to define the lead receiving cavity 82 into which the lead is positioned and the overmolding cavity 84 into which the mixture described above is added to be overmolded onto the lead.

It is noted that in FIG. 5D, in which the mold is depicted in the coupled configuration, the lower half 74A is depicted as a solid or opaque body, while the upper half 74B is schematically depicted as a transparent body in outlined form to allow depiction of the interior portions of the mold 70. It is understood, however, that an actual mold would typically be opaque.

Referring now to FIG. 5D, the lead receiving cavity 82 is a cavity in which the lead body 72 or a component thereof can be positioned as shown, while the overmolding cavity 84 is the cavity into which the liquid mixture can be injected or otherwise disposed to form the drug-eluting component over the lead body 72. It is understood that the shape of the lead receiving cavity 82 can be defined as desired to receive any of a variety of configurations of lead bodies to which one or more drug-eluting components are desired to be added. Similarly, it is understood that the shape of the overmolding cavity 84 can be defined as desired to produce any of a variety of configurations of drug-eluting components. For example, as described above, the resulting component can take the form of one or more plugs, strips, spirals, dots, tines, or any other known shapes or configurations that could be used to deliver a bioactive agent to the patient.

A mold such as the mold 70 depicted in FIGS. 5A-5F can be used in the following fashion, according to one embodiment. As shown in FIG. 5B, the lead body 72 to which the drug-eluting component is to be added is positioned in the first half 74A of the mold 70, and more specifically is positioned in the lead receiving cavity 78 as best shown in FIG. 5A. Alternatively, the lead body 72 can be positioned in the lead receiving cavity (not shown) of the second half 74B.

Once the lead body 72 is positioned as desired, the first half 74A and second half 74B are coupled together as best shown in FIGS. 5C and 5D such that the lead receiving recess 78 of the first half 74A is in communication with and matched up with the lead receiving recess (not shown) of the second half 74B to create the lead receiving cavity 82. Once the two halves 74A, 74B are successfully coupled, the mixture of precursor components (already mixed as described above) can be injected into the mold 70. In one embodiment as shown in FIGS. 5C-5F, the upper half 74B has a channel 86 in communication with the overmolding cavity 84 through which the precursor components can be injected into the cavity 84. As can be seen in these figures, the components are injected or otherwise placed through the channel 86 and into the overmolding cavity 84. As the components fill up the cavity 84, they surround and adhere to the lead body 72 or a component thereof at the two portions of the body 72 that are positioned in the cavity 84. It is understood that the lead body 72 or component thereof can be polymeric or metallic or any other material of a component of a lead body 72. Alternatively, the precursor components can be injected into the overmolding cavity 84 by any known mechanism or method.

Figure 6:
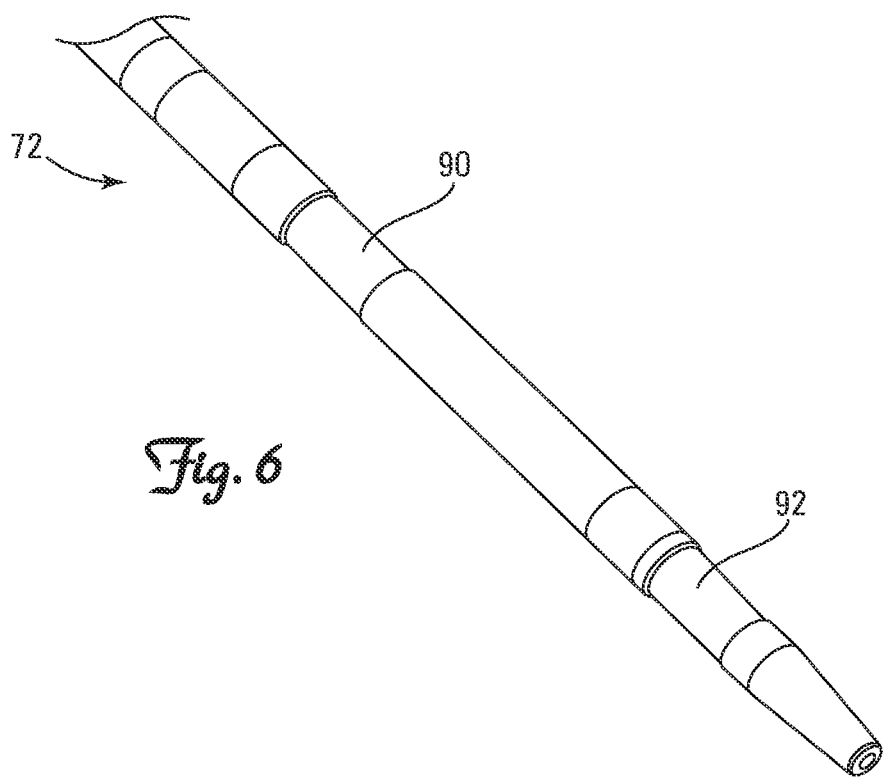
FIG. 6 is a perspective view of a lead body with two collars, according to one embodiment.

According to one implementation, the resulting lead body 72 has two overmolded drug collars 90, 92, as shown in FIG. 6.

In an alternative embodiment, the process can be used to overmold one collar or any other component configuration onto a lead body. Alternatively, it can be used to overmold two or more components onto the body. It is understood that any number of components could be positioned onto a lead body using the above process. To accomplish this, the mold can be configured to define an overmolding cavity at each desired location along the lead body receiving cavity to provide the desired number of components.

According to one embodiment, the process can involve two or more overmolding steps. That is, the process can include a first overmolding step that overmolds a first set of one or more components onto a lead body and a second overmolding step that overmolds a second set of one or more components that are positioned directly over the first set of components or in some overlapping configuration. Further, the process can include more than two overmolding steps, resulting in multiple components or components having multiple layers of overmolded material. In any embodiment in which two or more layers are added to create a layered component or multiple components, it is understood that one or more of the layers may contain a bioactive agent, while one or more of the layers may not. In a further embodiment, one or more of the layers could be a component that promotes adhesion, while one or more of the layers could control release of the bioactive agent in one or more of the other layers.

In a further implementation, it is further understood that the process described above can also be used to overmold one or more collars onto two or more lead bodies simultaneously. That is, the mold can be configured to define more than one lead body receiving cavity into which more than one lead body would be positioned. In this embodiment, the overmolding cavity is a single cavity that is in fluid communication with each of the lead body receiving cavities. Alternatively, the mold can have a separate overmolding cavity for each of the lead body receiving cavities.

Figure 7:
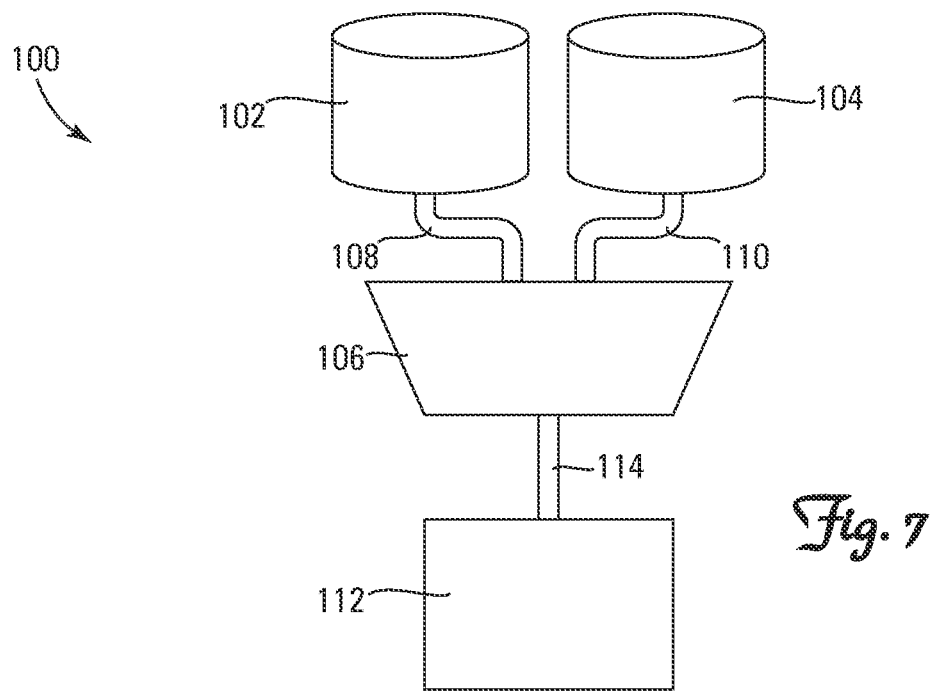
FIG. 7 is a schematic view of a liquid injection system, according to one embodiment.

In one embodiment as best depicted schematically in FIG. 7, a liquid injection system 100 is used to inject the mixture into the mold (not shown). In this embodiment, the liquid injection system 100 has a polymer container 102 and a bioactive agent container 104, which are in communication with a mixer 106 via lines 108, 110, respectively. Alternatively, the first container 102 receives a first polymer and bioactive agent and the second container 104 receives a second polymer and bioactive agent. Further, the mixer 106 is in communication with a press 112 via a line 114.

Alternatively, the system 100 can have a single container (instead of the separate polymer and bioactive agent containers) that receives the mixture of the polymer and bioactive agent. In such an embodiment, the components are mixed together prior to addition of the mixture to the container. For example, if there are two polymer components and a bioactive agent, the three components are mixed together prior to being added to the container.

In a further alternative, the system 100 can have three containers, including the first polymer component container, a second polymer component container, and the bioactive agent container. In this embodiment, the two polymer components are maintained in separate containers to prevent the polymer components from combining and beginning to cure. In one implementation having three containers, the first and second polymer containers can be positioned such that the two polymers are combined and mixed in a mixer and then the bioactive agent is added to that mixture and all three components are mixed together in a second mixer.

In use, a polymer is placed in the polymer container 102 and bioactive agent is placed in the bioactive agent container 104. Further, a mold (not shown), such as, for example, a mold similar to the mold embodiment described above, is positioned in the press 112, and the press 112 is actuated to retain the mold. The system 100 can then be actuated to use hydraulic pressure to push the polymer from the polymer container 102 along the line 108 into the mixer 106 and at the same time to push the bioactive agent from the bioactive agent container 104 along the line 110 into the mixer 106. The mixer 106 mixes the two components and the resulting mixture is pushed along the line 114 to the mold positioned in the press 112. The mixture is injected into the mold by forcing the mixture into the overmolding cavity (not shown) of the mold, as discussed above.

It is understood that any type of mold for use in such overmolding procedures could be used with the liquid injection system embodiments described herein.

The use of a liquid injection system 100 allows for a fast, efficient, consistent, and repeatable overmolding process that produces leads having one or more drug-eluting components with significantly reduced variation in dimensions and structure in comparison to drug-eluting components produced by prior art methods. It is understood that any known liquid injection system similar to the system 100 described above with respect to FIG. 7 could be used to produce the drug-eluting components described herein.

Alternatively, a transfer overmolding process can be utilized in which the mixture can be inserted into a mold via known methods using a transfer press. In this embodiment, the mold is positioned in the transfer press, and then the mixture is transferred from a mixer to a transfer apparatus. In this embodiment, the transfer apparatus is a syringe-like apparatus with a plunger. The transfer apparatus is then coupled to the mold and the mixture is injected into the mold.

In yet another alternative, one or more drug-eluting components can be placed on a lead body by any known injection or compression method. Further, any known method can be used for producing the drug-eluting components as described herein and placing them on a lead body.

Once the mixture has been injected into the mold, the lead and the drug-eluting component are allowed to cure before the lead with the component is removed from the mold. In this embodiment, the mold is heated to apply heat to the liquid mixture in the mold, which speeds up the curing process.

In one implementation utilizing a transfer molding process, the curing period in the heated mold can range from about 15 minutes to about 1 hour. In another transfer molding embodiment, the heat applied during the curing period can range from about 80° to about 200° C.

In another implementation utilizing a liquid injection molding process, the curing period can range from about 1 second to about 1 hour. Alternatively, the curing period can range from about 10 seconds to about 1 minute. In another liquid injection embodiment, the heat applied during the curing period can range from about 100° to about 200° C.

When the curing period is complete, the lead having at least one drug-eluting component can be removed from the mold.

In an alternative embodiment, the one or more drug-eluting components need not be overmolded onto the lead body. That is, the one or more drug-eluting components could instead be created by a molding process similar to that described above (without the overmolding step) in a process called "premolding" and then can be physically positioned on the lead body by any known application method.

As discussed above, according to various embodiments, in use, a drug eluting lead can be delivered to a desired site within the patient's body. Once implanted, the bioactive agent may elute from the surface of the implant and diffuse into the adjoining tissue. In this manner, the inflammatory process and/or other unwanted biological processes associated with implantation and the presence of the foreign object can be suppressed (e.g., reduced inflammation and/or toxicity of inflammatory response). Alternatively, the growth of non-excitable, connective tissue around the electrode (e.g., the fibrotic capsule) can be reduced (e.g., a reduction in fibrotic capsule thickness may be observed), and thus, the postoperative rise in the stimulation threshold lessens, and a stable reduced threshold, both acute and chronic, is thereby provided. In yet another alternative, the drug eluting devices disclosed herein can also facilitate extraction of the lead body due to lower fibrous capsule formation. Additionally, the device and methods may prevent myocyte cell function impairment and/or necrosis around, near or on an electrode, which may further stabilize a reduced threshold.

In accordance with a further embodiment, a drug-eluting component as described herein can be overmolded onto a portion of a lead body having a patterned surface. In another embodiment, the drug-eluting component can be overmolded or otherwise positioned onto a portion of a lead body in a patterned configuration such that the drug-eluting component itself creates or is a part of the patterned surface. As used herein, the term "patterned surface" or "patterned lead body surface" shall mean any pattern of steps and/or gaps or other machined features on the surface of a lead body.

Figure 8A:
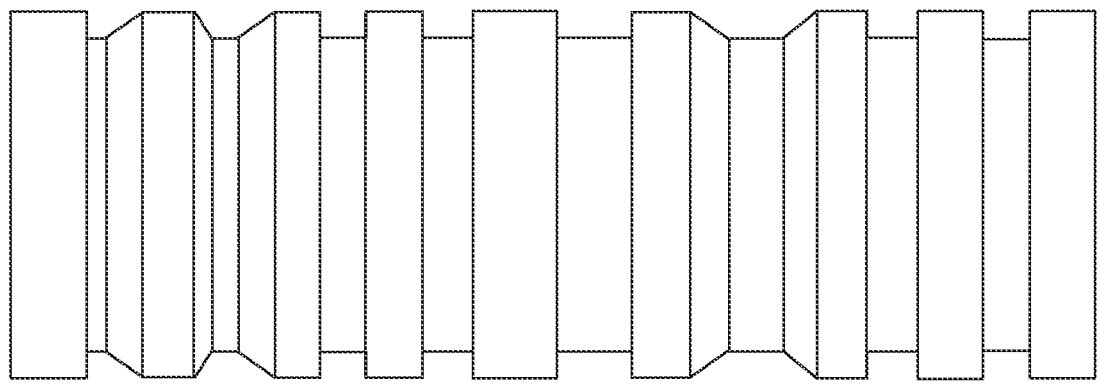
FIG. 8A is a side view of a patterned lead body surface, according to one embodiment.
Figure 8B:
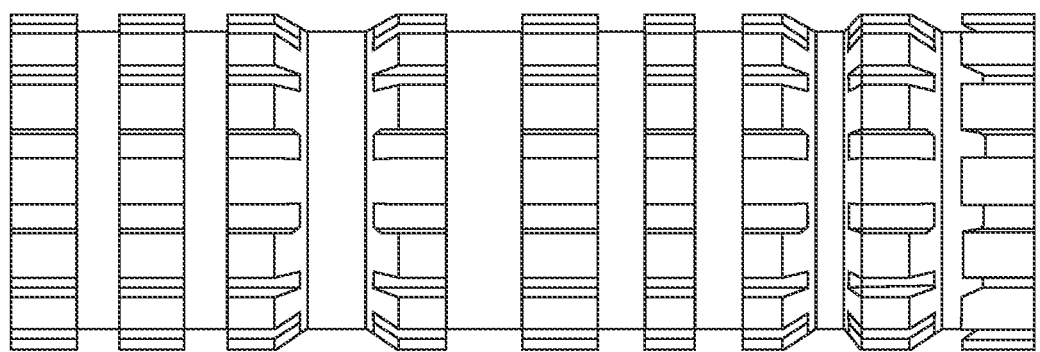
FIG. 8B is a side view of another patterned lead body surface, according to another embodiment.

FIGS. 8A and 8B depict two exemplary embodiments of patterned lead body surfaces. It is understood that these are non-limiting embodiments and that any pattern of machined features on a lead body surface can be utilized.

According to one implementation, the outer surface of a lead body comprised of an appropriate substrate can be surfaced by any known laser cutting process. For example, in one embodiment a lead body comprising polyurethane or silicone rubber is surfaced using a laser cutting process. In this process, laser energy is used to selectively remove material from the polyurethane or silicone rubber tubing substrate to create a patterned surface.

Figure 8C:
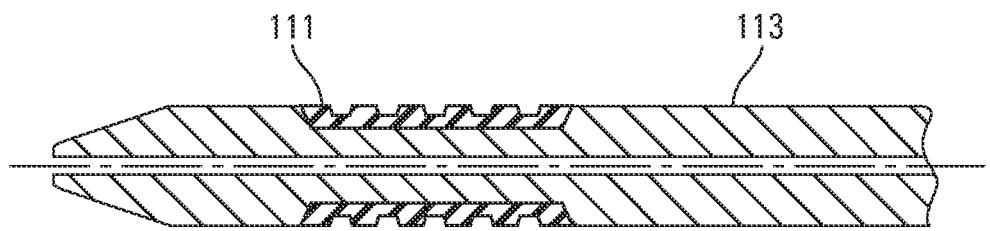
FIG. 8C is a cross-sectional view of an overmolded patterned lead body surface, according to one embodiment.
Figure 8D:
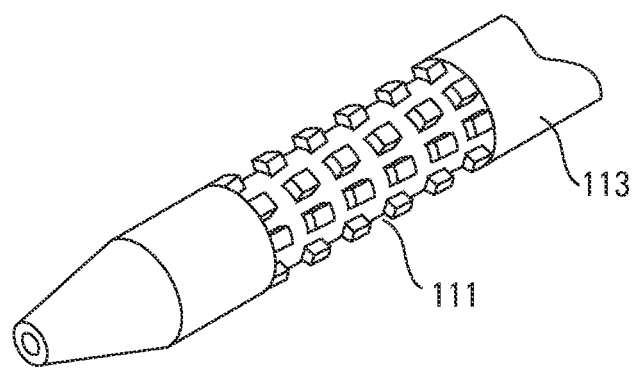
FIG. 8D is a perspective view of the overmolded patterned lead body surface of FIG. 8C, according to one embodiment.

In accordance with another embodiment, a patterned surface can be created on a lead body by an overmolding process. That is, the patterned surface can be overmolded onto the lead body by any known overmolding process. For example, FIGS. 8C and 8D depict an alternative implementation of a patterned lead body surface in which the surface is an overmolded surface 111. In this embodiment, the surface 111 is molded over the lead body 113 and is a patterned surface 111 of steps and gaps. In one implementation, the material molded over the lead body 113 to create the patterned surface contains a bioactive agent. Alternatively, the material contains no bioactive agent.

Alternatively, any known surface machining process can be utilized for creating a patterned surface. In one embodiment, a machining process can be used to machine a patterned surface onto a lead body made of any appropriate metal or machinable polymer. In one example, a known device such as a Swiss screw machine or similar equipment can be used to remove material from a substrate, thereby creating a patterned surface on the lead body.

In yet another alternative, any known patterning process, such as, for example, positive stamping, spray patterning, chemical etching, or masking, can be used to create a patterned surface on a lead body.

In certain embodiments as described above, a patterned surface as described herein can be configured to receive a drug-eluting component. Alternatively, the patterned surface is incorporated into a lead body without a drug-eluting component.

It is understood that the patterned surface can be located anywhere on the lead body. In one embodiment, the patterned surface is located at the distal tip of the lead body. Alternatively, the patterned surface is positioned at the distal tip and along some length of the body proximal to the distal tip as well. In a further alternative, the patterned surface is positioned anywhere along the lead body.

Figure 9:
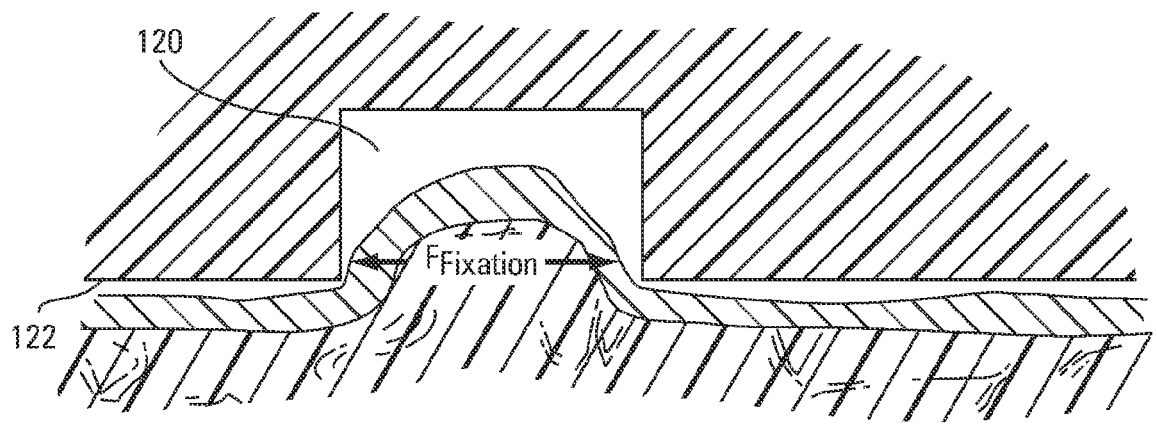
FIG. 9 is a schematic view of a patterned feature on a lead body surface, according to one embodiment.

One possible benefit of a patterned lead body surface is enhanced fixation, according to one embodiment. That is, the increased surface roughness created by the patterned surface may increase the friction or traction between the lead body surface and the vein wall. This increased friction or traction can result in improved fixation of the lead body to the wall. Another way in which the patterned surface may enhance fixation is through micro adhesion and tissue in-growth. For example, FIG. 9 depicts a single exemplary patterned feature 120 on a lead body surface 122. In this embodiment, the wall tissue begins to grow into the feature 120. Similarly, such ingrowth could occur in many recesses along a patterned surface, thereby enhancing fixation of the lead to the wall.

This fixation enhancement could be beneficial for any lead in which tissue fixation aids operability or usability of the lead. In addition, the enhancement may be especially effective for leads with bias tips (i.e. high normal force on the vein wall), such as the ACUITY Spiral™, which is available from Boston Scientific.

In embodiments in which the patterned surface provides enhanced fixation, the patterned surface can be positioned anywhere along the lead body where fixation is beneficial. For example, in one embodiment in which fixation at the distal tip of the lead body is desirable, the distal tip has a patterned surface. Alternatively, if fixation is desirable along some length of the lead body, that length can have a patterned surface.

Figure 10:
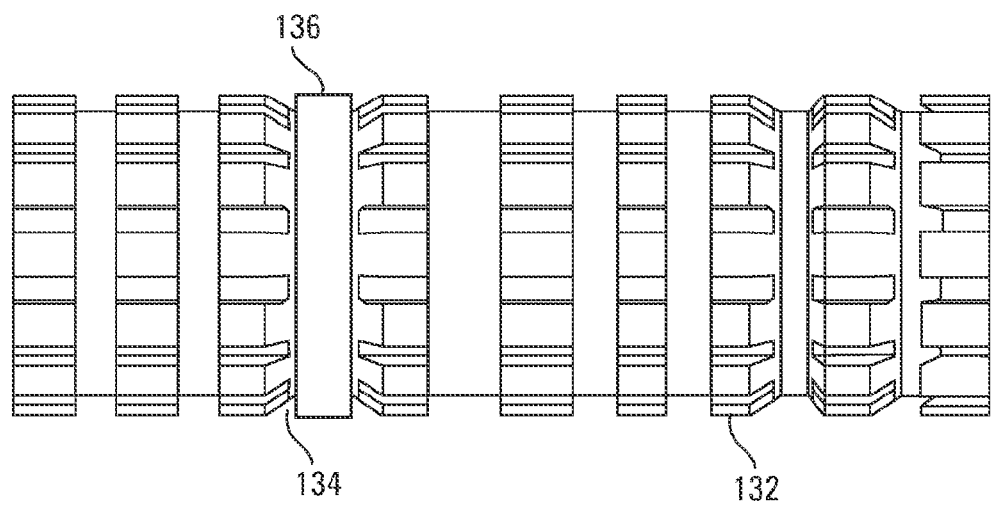
FIG. 10 is a side view of a patterned lead body surface with an overmolded drug-eluting component, according to one embodiment.

Alternatively, another possible benefit of a patterned lead body surface is that a portion of the patterned surface can be used as a recess for receiving any overmolded drug-eluting component embodiment as described above. For example, as shown in FIG. 10, a lead body 130 has a patterned surface 132 (similar to the patterned surface of FIG. 8B) having a defined recess 134 configured to receive an overmolded drug-eluting component 136. It is understood that the component 136 can be overmolded into the recess 134 according to any method described herein. Alternatively, it is further understood that the component 136 could also be molded separately and physically positioned on the lead body 130.

According to various implementations, any patterned lead body surface can have a recess configured to receive an overmolded drug-eluting component. In certain embodiments, the recess in which the drug-eluting component is positioned is the only portion of the surface that is patterned, such that the remainder of the lead body surface is smooth or un-patterned. Alternatively, other portions of the lead body surface are patterned as well.

In a further alternative of an overmolded patterned surface, instead of overmolding a drug-eluting component into the patterned recesses of the patterned surface, the bioactive agent can be incorporated into the overmolded patterned surface such that the patterned surface itself is a drug-eluting component and thus no separate drug-eluting component is needed. In this embodiment, the overmolded patterned surface component is a combination of a polymer and a bioactive agent. The polymers and bioactive agents used can be any of those described above in connection with other embodiments.

In this embodiment in which the overmolded patterned surface component is a drug-eluting component, the patterned surface can provide the benefit of enhanced fixation as described above, while the bioactive agent being eluted from the component can provide the benefits of drug-eluting components described above.

In a further alternative implementation, a portion of the patterned surface can be a drug-eluting component and a portion of the patterned surface can be a non-drug-eluting composition.

Another possible benefit of lead body surface patterning is the ability to impact and/or control the lead body stiffness. That is, the lead track patterning of the body surface can be used to influence the lead body stiffness. For example, a particular pattern or configuration could be applied to a lead body surface—either internal or external—to enhance the stiffness of the lead body. Alternatively, a different pattern or configuration could be applied to an internal or external lead body surface to reduce the lead body stiffness. It is understood that this stiffness control can include influence over bending, axial, and/or torsional stiffness of the lead body, depending on the design of the body and the patterned surface.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of forming an implantable medical electrical lead having an elongated polymeric body with an outer surface, the method comprising:
   forming a plurality of longitudinally spaced circumferential slots in the outer surface of the lead body, each slot defined by polymeric material of the elongated polymeric body, each slot formed by removing polymeric material from the elongated polymeric body such that the slot extends radially inwardly from the outer surface of the elongated polymeric body; and
   overmolding a first drug-eluting component at least partially within a first of the longitudinally spaced circumferential slots.

2. The method of claim 1, wherein removing the polymeric material from the elongated polymeric body comprises machining each slot from the elongated polymeric body.

3. The method of claim 1, wherein forming the plurality of longitudinally spaced circumferential slots includes applying laser energy to selectively remove material from the outer surface of the lead body.

4. The method of claim 1, wherein overmolding the drug-eluting component comprises positioning the lead body in a mold and injecting a polymer matrix including a bioactive agent into the mold.

5. The method of claim 4, wherein injecting the polymer matrix comprises injecting the polymer matrix using a liquid injection system.

6. The method of claim 4, wherein injecting the polymer matrix comprises injecting the polymer matrix using a transfer press.

7. The method of claim 1, further comprising overmolding a second drug-eluting component at least partially within a second of the patterned recesses.

8. A method of forming an implantable medical electrical lead having an elongated polymeric body, the method comprising:
   disposing a first drug-eluting polymeric component on the outer surface of the lead body; and
   molding a patterned surface on an outer surface of the first drug-eluting polymeric component, the patterned surface comprising a plurality of longitudinally spaced circumferential slots formed within the first drug-eluting polymeric component, each circumferential slot extending radially inwardly from the outer surface of the first drug-eluting polymeric component.

9. The method of claim 8, wherein the patterned surface enhances fixation of the implantable medical electrical lead by increasing one or both of friction and traction between the outer surface and a vein wall.

10. A method of forming an implantable medical electrical lead having an elongated polymeric body with an outer surface, the method comprising:
    forming a lead body, the lead body having a circumferential slot formed within polymeric material of the elongated polymeric body, the circumferential slot extending radially inwardly from the outer surface of the elongated polymeric body;
    placing the lead body along a lead receiving cavity of a mold such that the recess of the lead body is within the mold;
    mixing a polymer and a drug together; and
    forming an overmolded drug-eluting component within the slot of the lead body from the mixture of the polymer and the drug.

11. The method of claim 10, wherein the overmolded drug-eluting component comprises a patterned surface.

12. The method of claim 11, wherein the patterned surface is configured to enhance fixation of the lead body to tissue by growth of the tissue into the patterned surface.

13. The method of claim 11, wherein the patterned surface comprises a plurality of circumferential slots.

14. The method of claim 13, wherein the patterned surface further comprises a plurality of longitudinal slots overlapping the plurality of circumferential slots.

15. The method of claim 11, wherein the patterned surface is configured to selectively affect a stiffness of the lead body.

16. The method of claim 10, wherein the slot comprises a plurality of longitudinally spaced circumferential slots and forming the overmolded component comprises forming the overmolded component over the plurality of longitudinally spaced circumferential slots.

17. The method of claim 10, wherein the overmolded drug-eluting component is a collar.

18. The method of claim 10, wherein the overmolded drug-eluting component elutes an agent that suppresses one or both of an inflammatory response and unwanted biological processes associated with implantation.

19. The method of claim 10, wherein the overmolded drug-eluting component elutes an agent that reduces tissue growth.

20. The method of claim 10, wherein the polymer and the drug are mixed with a drug-to-polymer ratio in the range of 1:50 to 1:1.

21. The method of claim 10, wherein the recess in the outer surface of the lead body comprises a slot extending around the circumference of the lead body.

22. A method of forming an implantable medical electrical lead having an elongated polymeric body, the method comprising:
   forming a lead body;
   placing the lead body along a lead receiving cavity of a mold such that a recess of the lead body is within the mold, the recess defined by polymeric material of the elongated polymeric body;
   mixing a polymer and a drug together;
   injecting the mixture of the polymer and the drug into the mold to overmold a drug-eluting component over the recess; and
   forming a patterned surface on an exterior surface of the lead from the drug-eluting component formed from the injected mixture, the patterned surface comprising a plurality of longitudinally spaced circumferential slots formed within the drug-eluting component and extending radially inwardly from an outer surface of the drug-eluting component.

23. A method of forming an implantable medical electrical lead having an elongated polymeric body with an outer surface, the method comprising:
   molding a plurality of longitudinally spaced circumferential slots in polymeric material, each slot extending radially inwardly from the outer surface of the elongated polymeric body;
   placing the lead body along a lead receiving cavity of a mold such that the plurality of slots of the lead body are within the mold;
   mixing a polymer and a drug together;
   injecting the mixture of the polymer and the drug into the mold; and
   forming an overmolded drug-eluting component within the plurality of slots from the injected mixture of the polymer and the drug.

* * * * *